United States Patent [19]

Chen

[11] 4,291,055

[45] Sep. 22, 1981

[54] INSECTICIDAL PHENOXY HYDROXAMATES

[75] Inventor: Albert C. Chen, East Brunswick, N.J.

[73] Assignee: Mobil Oil Corporation, New York, N.Y.

[21] Appl. No.: 109,693

[22] Filed: Jan. 4, 1980

[51] Int. Cl.³ .................. A01N 37/28; C07C 83/10
[52] U.S. Cl. ......................... 424/298; 260/453 RW
[58] Field of Search ............... 260/453 RW; 424/298

[56] References Cited

U.S. PATENT DOCUMENTS 3,890,377 6/1975 Marshall ................. 260/453 RW
4,024,163 5/1977 Elliott et al. ................. 260/347.4
4,062,968 12/1977 Fujimoto et al. ................. 549/58

OTHER PUBLICATIONS

P. E. Berteau, et al., J. Agr. Food Chem. 17, #5, p. 931 (1969).

Primary Examiner—Henry R. Jiles
Assistant Examiner—Robert C. Whittenbaugh
Attorney, Agent, or Firm—Charles A. Huggett; Michael G. Gilman; Hastings S. Trigg

[57] ABSTRACT

3-Phenoxybenzyl hydroxamates of pyrethroid acids and derivatives are insecticidal.

18 Claims, No Drawings

INSECTICIDAL PHENOXY HYDROXAMATES

BACKGROUND OF THE INVENTION

1. Field of the Invention

This invention is directed to certain hydroxamates having insecticidal activity.

2. Description of Prior Art

Several synthetic pyrethroid esters have been described in the literature as potent insecticides; e.g. U.S. Pat. Nos. 4,062,968 and 4,024,163. The literature further teaches us that analogous compounds replacing the carboxylate moiety with a carboxamido group are weakly insecticidal (P. E. Berteau and J. E. Casida, J. Agr. Food Chem. 17 #5, pg. 931 (1969). The insecticidal activity of the compounds of this invention, likewise containing a carboxamido moiety, is therefore unexpected and novel.

SUMMARY OF THE INVENTION

This invention provides insecticidal hydroxamates having the formula:

$$R^1-\underset{\underset{R^2}{|}}{\overset{\overset{O}{\|}}{C}}-N-O-\underset{\underset{H}{|}}{\overset{\overset{R^3}{|}}{C}}H-\text{(3-phenoxyphenyl)}$$

wherein $R^1$ may represent I, II, III, or IV.

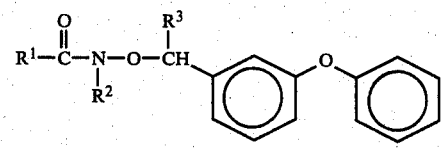

I, II, III, IV wherein Ar is phenyl; phenyl substituted in the 2-to-6 position with 1–5 halogen (Cl, Br, F, I), $C_1$–$C_4$ alkyl, amino alkylamino, dialkylamino, alkoxy, methylenedioxy alkylthio, trifluoromethyl, trifluoromethoxy, difluoromethoxy, trifluorothiomethyl, difluorothiomethyl, haloalkyl, alkylthioalkyl, alkenyl, alkynyl, cyano, cyanoalkyl, carboalkoxy, alkylsulfonyl, alkoxyalkyl, haloalkenyl, acyl, indanyl or naphthalyl; Z is $C_2$–$C_4$ alkyl, $C_3$–$C_6$ cycloalkyl, alkylcycloalkyl or $C_2$–$C_4$ alkenyl. Y is F, Cl, or Br; and $R^2$ and $R^3$ are the same or different H, alkyl, CN, CHO, C≡CH, $CH_2C≡CH$ $CH_2CH=CH_2$, $CH_2O$-alkyl, $CH_2S$-alkyl, or S-alkyl; alkyl being $C_1$–$C_4$; and II saturated on the vinyl group with Br.

DESCRIPTION OF SPECIFIC EMBODIMENTS

Non-limiting examples of the compounds of this invention include:

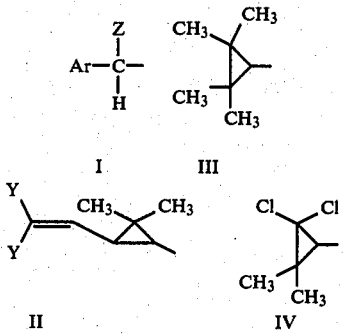

| X | $R^2$ | $R^3$ | Z |
|---|---|---|---|
| $F_3CO$ | H | H | △ |
| $F_3CS$ | H | H | isopropyl |
| F | H | H | isopropyl |
| Br | H | H | △ |
| $F_3C$ | H | H | △ |
| $F_3CO$ | $C_2H_5$ | H | isopropyl |
| $F_3CS$ | CHO | H | △ |
| $F_2ClC$ | $CH_3$ | H | △ |
| Cl | H | CN | isopropyl |
| Cl | H | C≡CH | isopropyl |

$$\underset{\underset{CH_3}{|}}{\overset{\overset{CH_3}{|}}{C}}\text{-cyclopropyl-}C(=NO-)\underset{R^2}{}\overset{R^3}{-}CH\text{-(3-phenoxyphenyl)}$$

| $R^2$ | $R^3$ |
|---|---|
| H | CN |
| H | CHO |
| H | $CH_2C≡CH$ |
| $CH_2C=CH_2$ | H |
| $CH_2OCH_3$ | H |
| $SCH_2CH_3$ | H |
| H | $CH_3$ |

$$Y_2C=CH\text{-cyclopropyl-}C(=NOR^2)\text{-O-}CH(R^3)\text{-(3-phenoxyphenyl)}$$

| Y | $R^2$ | $R^3$ |
|---|---|---|
| F | H | H |
| F | $CH_3$ | H |
| Br | H | H |
| Cl | H | $CH_2OCH_3$ |
| Cl | H | $CH_2SCH_2CH_3$ |
| Cl | $CH_3$ | CN |
| Cl | $CH_2CH_3$ | H |
| Cl | $CH_2OCH_3$ | H |

In general, the compounds of this invention can be prepared using known amidification reaction between the acid chloride of the carboxylic acid reactant, preferably in the presence of a tertiary amine HCl acceptor, with a 3-phenoxybenzyloxyamine reactant. The 3-phenoxybenzyloxyamine reactant can be prepared according to the general procedure described in Bull. De L'Academie Polonaise Des Sciences, Vol. XXII, #3, pg. 195 (1974).

Alternatively, these compounds can be prepared by reacting the hydroxamic acid of the carboxylic acid reactant with 3-phenoxybenzyl chloride or bromide, or a derivative thereof substituted on the methylene group ($R^3$), in the presence of $K_2CO_3$. The hydroxamic acid can be prepared by reacting the acid chloride of the carboxylic acid reactant with hydroxylamine, using a tertiary amine HCl acceptor.

The general preparation of the carboxylic acid reactants of this invention is described in the following U.S. Pat. Nos. 4,024,163, 4,062,968 and 4,137,324, which are incorporated herein by reference.

In the following examples, the preparation and use of the compounds of this invention are demonstrated. All parts are by weight.

Starting Materials

Examples of the synthesis of compounds of this invention are the following:

1. Acid chlorides

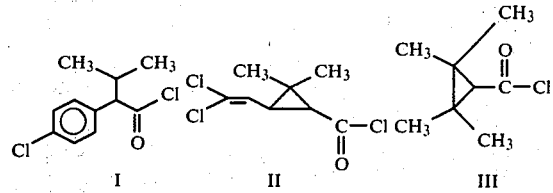

2. Hydroxamic acids

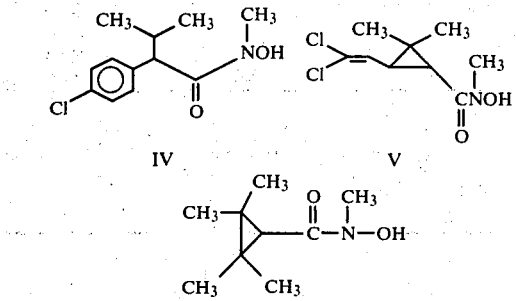

3. O—Alkyl hydroxylamines

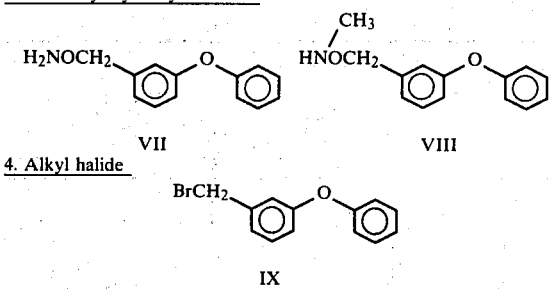

4. Alkyl halide

BrCH₂—⌬—O—⌬

IX

SYNTHETIC PROCEDURES

EXAMPLE 1

Acid chloride (I, 1.4 parts) in 10 parts of benzene was added, in 45 min., into a solution comprising 1.3 parts of the O-alkyl hydroxylamine (VII), 0.7 part of triethylamine and 10 parts of benzene. During the addition, temperature was moderated by a cold water bath and the reaction mixture was then stirred at room temperature for 2 hrs. Ether was added and the solution washed with water. Subsequent work-up yielded 2.0 parts of the product.

EXAMPLE 2

The hydroxamic acid (IV, 1.00 part), the bromide (IX, 1.05 parts), $K_2CO_3$ (1.10 parts) and acetone (25 parts) were refluxed for 24 hrs. After cooling to room temperature, solids were removed and the filtrate evaporated. The residue was dissolved in ether and washed with brine solution. A usual work-up procedure gave 1.7 parts of the product.

EXAMPLE 3

Into a solution containing 1.2 parts of VII, 0.6 part of triethylamine and 10 parts of benzene was added 0.9 part of the acid chloride (III) in 10 parts of benzene. The reaction mixture was stirred at room temperature overnight. Solids were removed. The filtrate was mixed with ether, washed with water and dried. After work-up, it gave 1.3 parts of the product.

EXAMPLE 4

The hydroxamic acid (VI, 1.70 parts), alkyl bromide (IX, 2.63 parts), $K_2CO_3$ (2.76 parts) and acetone (30.0 parts) were refluxed overnight. Solids were filtered and washed with ether. The filtrate was evaporated and redissolved in ether. The ethereal solution was washed with 5% NaOH solution and water. After drying and evaporation, the residue was chromatographed on silica gel giving pure products.

EXAMPLES 5 AND 6

The acid chloride (II, 1.01 parts, consisted of a mixture of cis- and trans-isomers) in 5 parts of benzene was added into a solution containing 0.90 part of the amine VII, 0.42 part of triethylamine and 5.0 parts of benzene. The addition was complete in 20 min. and the reaction mixture stirred at room temperature for 2 hrs. Solids were removed and the filtrate washed with water. After evaporation, the crude product was chromatographed on silica gel to give 0.4 part of pure cis-isomer and 0.4 part of pure trans-isomer of the product.

EXAMPLES 7 AND 8

The hydroxamic acid (V, 1.0 part, containing both the cis- and the trans-isomers), 0.9 part of IX, 1.0 part of $K_2CO_3$ and 25 parts of acetone were refluxed overnight. After cooling, solids were filtered and the filtrate evaporated. The residue was chromatographed to give pure cis-isomer and trans-isomer.

EXAMPLE 9

The acid chloride (II, 60% cis) in $CCl_4$ solution was brominated to saturate the vinyl double bond, using known bromination technique. Then, the brominated acid chloride was reacted as described in Examples 5 and 6 to give the brominated derivative of the compound of Examples 5 and 6. The product was not chromatographed.

The compounds of this invention have been found to exhibit considerable biological activity. They are especially potent pesticides when used to control or combat important agricultural pests. These compounds can be used in various ways to achieve biological action. They can be applied per se, as solids or in vaporized form, but are preferably applied as the toxic components in pesticidal compositions of the compound and a carrier. The compositions can be applied as dusts, as liquid sprays, or as gas-propelled sprays and can contain, in addition to a carrier, additives such as emulsifying agents, wetting agents, binding agents, gases compressed to the liquid state, odorants, stabilizers and the like. A wide variety of liquid and solid carriers can be used in the pesticidal compositions. Non-limiting examples of liquid carriers include water; organic solvents such as alcohols, ketones, amides, and esters; mineral oils such as kerosene, light oils, and medium oils, and vegetable oils such as cottonseed oil. Non-limiting examples of solid carriers include talc, bentonite, diatomaceous earth, pyrophyllite, fullers earth, gypsum, flours derived from cottonseeds and nut shells, and various natural and synthetic clays having a pH not exceeding about 9.5.

The amount of the compounds of this invention utilized in pesticidal compositions will vary rather widely. It depends to some extent upon the type of composition in which the material is being used, the nature of the condition to be controlled, and the method of application (i.e., spraying, dusting, etc.). In the ultimate pesticidal composition, as applied in the field, pesticide concentrations as low as 0.0001 weight percent of the total composition can be used. In general, compositions, as applied, containing about 0.05 weight percent pesticide in either liquid or solid carrier, give excellent results. In some cases, however, stronger dosages up to about 10 weight percent may be required.

In practice, pesticidal compositions are usually prepared in the form of concentrates, which are diluted in the field to the concentration desired for application. For example, the concentrate can be a wettable powder containing large amounts of the compound of this invention, a carrier (e.g. attapulgite or other clay), and wetting and dispersing agents. Such powders can be diluted prior to application, by dispersing it in water to obtain a sprayable suspension containing the concentration of pesticide desired for application. Other concentrates can be solutions that can be later diluted, e.g. with kerosene. Thus, it is within the contemplation of this invention to provide pesticidal compositions containing up to about 80 percent, by weight of the composition, of a pesticidal compound of this invention. Accordingly, depending upon whether it is ready for application or it is in concentrated form, the contemplated pesticidal compositions contain between about 0.0001 percent and about 80 percent, by weight of the compositions, of a pesticidal compound of this invention and a carrier, liquid or solid, as defined hereinbefore.

INSECTICIDE TEST METHODS

Bait Test [Housefly (Adult)]

Method of Treatment

One milliliter of an aqueous solution or suspension of the candidate compound is pipetted into a 9 cm. petri dish containing filter paper and 0.1 gm. granular sugar. Ten adults are admitted and the dish is closed.

Method of Recording Results

Mortality is recorded after 24–75 hours. Compounds which produce 90% mortality are reevaluated at lower concentrations in secondary tests. Mode of action may be by stomach poison, contact or vapor.

Stomach Poison—Foliar Dip Test

Primary Screen
  Southern Armyworm (Larva)
  Mexican Bean Beetle (Larva)

Method of Treatment

Lima bean leaves of a uniform size are momentarily dipped in a 500 ppm. water-acetone of the test material. Treated leaves are placed on moistened filter paper in 9 cm. petri dishes and allowed to air dry, and then are infested. The dishes are then closed.

Method of Recording Results

Mortality is recorded 72 hours after infestation. Compounds active at 500 ppm. are retested at 100 and 10 ppm. All test results are recorded as percent control. In the tabulation of data, the insect species are abbreviated as follows: Housefly (HF), Mexican Bean Beetle (MB), and Southern Armyworm (SA).

The compounds of Examples 1 through 9 were subjected to the aforedescribed insecticide tests. Test concentrations and results are set forth in the Table, along with structural formulae for convenient reference.

TABLE

| STRUCTURE | RATE (ppm) | Percent Control HF | SA | MB |
|---|---|---|---|---|
| EXAMPLE 1 | 500 / 100 / 10 | 50 / — / — | 90 / 75 / — | 100 / 85 / 20 |
| EXAMPLE 2 | 500 / 100 / 10 | 80 / 5 / 0 | 100 / 50 / 0 | 100 / 95 / 55 |
| EXAMPLE 3 | 500 / 100 / 10 | 90 / 15 / 0 | 60 / — / — | 100 / 45 / — |
| EXAMPLE 4 | 500 / 100 / 10 | 0 / — / — | 0 / — / — | 40 / — / — |
| EXAMPLE 5 (100% cis) | 500 / 100 / 10 | 100 / 100 / 10 | 100 / 100 / 45 | 100 / 100 / 85 |

| STRUCTURE | RATE (ppm) | Percent Control | | |
|---|---|---|---|---|
| | | HF | SA | MB |
| 100% trans EXAMPLE 6 | 500 100 10 | 100 60 5 | 100 85 0 | 90 70 10 |
| 100% cis EXAMPLE 7 | 500 100 10 | 80 15 0 | 100 95 20 | 80 35 10 |
| 100% trans EXAMPLE 8 | 500 100 10 | 0 0 0 | 100 0 0 | 50 15 0 |
| Mixed cis and trans | 500 100 10 | 100 85 0 | 100 95 0 | 100 85 20 |

EXAMPLE 9

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. Insecticidal hydroxamates having the formula:

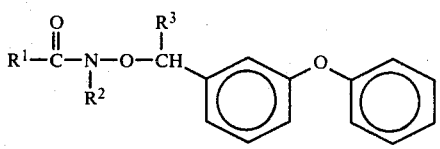

wherein $R^1$ may represent I, II, III, or IV:

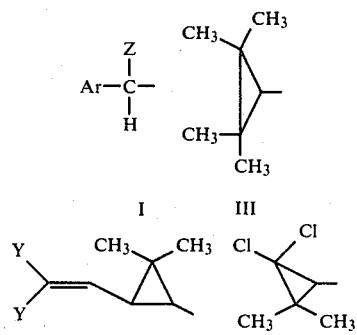

wherein Ar is phenyl; phenyl substituted in the 2-to-6 position with 1-5 halogen (Cl, Br, F, I), $C_1$-$C_4$ alkyl, amino, $C_1$-$C_4$ alkylamino, $C_1$-$C_4$ dialkylamino, $C_1$-$C_4$ alkoxy, methylenedioxy, $C_1$-$C_4$ alkylthio, trifluoromethyl, trifluoromethoxy, difluoromethoxy, trifluorothiomethyl, difluorothiomethyl, $C_1$-$C_4$ haloalkyl, $C_1$-$C_4$ alkylthioalkyl, $C_2$-$C_4$ alkenyl, $C_2$-$C_4$ alkynyl, cyano, $C_1$-$C_4$ cyanoalkyl, $C_1$-$C_4$ carboalkoxy, $C_1$-$C_4$ alkylsulfonyl, $C_1$-$C_4$ alkoxyalkyl, $C_1$-$C_4$ haloalkenyl, $C_1$-$C_4$ acyl, indanyl or naphthalyl; Z is $C_2$-$C_4$ alkyl, $C_3$-$C_6$ cycloalkyl, alkylcycloalkyl or $C_2$-$C_4$ alkenyl; Y is F, Cl, or Br; and $R^2$ and $R^3$ are the same or different H, alkyl, CN, CHO, C≡CH, $CH_2$C≡CH $CH_2$CH≡$CH_2$, $CH_2$O-alkyl, $CH_2$S-alkyl, or S-alkyl; alkyl being $C_1$-$C_4$; and II saturated on the vinyl group with Br.

2. A hydroxamate of claim 1 having the formula:

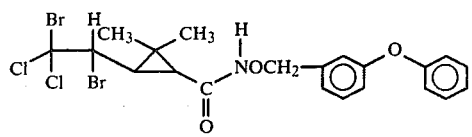

3. A hydroxamate of claim 1 having the formula:

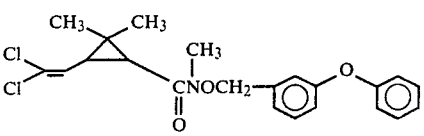

4. A hydroxamate of claim 1 having the formula:

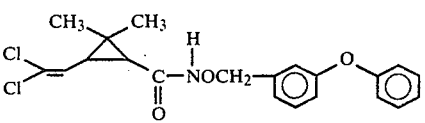

5. A hydroxamate of claim 1 having the formula:

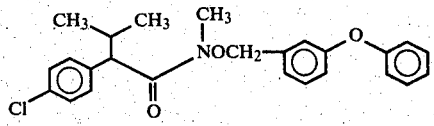

6. A hydroxamate of claim 1 having the formula:

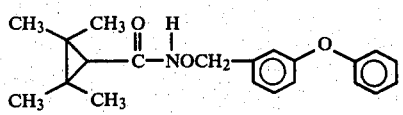

7. An insecticidal composition comprising a carrier and an insecticidal amount of a compound of claim 1.

8. An insecticidal composition comprising a carrier and an insecticidal amount of a compound of claim 2.

9. An insecticidal composition comprising a carrier and an insecticidal amount of a compound of claim 3.

10. An insecticidal composition comprising a carrier and an insecticidal amount of a compound of claim 4.

11. An insecticidal composition comprising a carrier and an insecticidal amount of a compound of claim 5.

12. An insecticidal composition comprising a carrier and an insecticidal amount of a compound of claim 6.

13. The method of combatting insects that comprises contacting them with an insecticidal amount of a compound of claim 1.

14. The method of combatting insects that comprises contacting them with an insecticidal amount of a compound of claim 2.

15. The method of combatting insects that comprises contacting them with an insecticidal amount of a compound of claim 3.

16. The method of combatting insects that comprises contacting them with an insecticidal amount of a compound of claim 4.

17. The method of combatting insects that comprises contacting them with an insecticidal amount of a compound of claim 5.

18. The method of combatting insects that comprises contacting them with an insecticidal amount of a compound of claim 6.

* * * * *